(12) United States Patent
Wilson

(10) Patent No.: US 10,925,306 B2
(45) Date of Patent: Feb. 23, 2021

(54) SYSTEMS AND METHODS FOR QUANTIFYING CALORIE VALUES FOR A PLURALITY OF DIFFERENT CALORIC FOOD CATEGORIES

(71) Applicant: Joshua P. Wilson, Denver, CO (US)

(72) Inventor: Joshua P. Wilson, Corpus Christi, TX (US)

( * ) Notice: Subject to any disclaimer, the term of this patent is extended or adjusted under 35 U.S.C. 154(b) by 187 days.

(21) Appl. No.: 16/317,169

(22) PCT Filed: Jul. 12, 2016

(86) PCT No.: PCT/US2016/041869
§ 371 (c)(1),
(2) Date: Jan. 11, 2019

(87) PCT Pub. No.: WO2018/013085
PCT Pub. Date: Jan. 18, 2018

(65) Prior Publication Data
US 2019/0313684 A1 Oct. 17, 2019

(51) Int. Cl.
*A23L 33/00* (2016.01)
*G09B 19/00* (2006.01)
*B65D 5/42* (2006.01)

(52) U.S. Cl.
CPC ............ *A23L 33/30* (2016.08); *B65D 5/4212* (2013.01); *G09B 19/0092* (2013.01); *B65D 2203/06* (2013.01); *B65D 2203/12* (2013.01)

(58) Field of Classification Search
CPC ....... A23L 33/00; A23L 33/30; B65D 5/4212; B65D 2203/06; B65D 2203/12; G09B 19/00; G09B 19/0092
See application file for complete search history.

(56) References Cited

U.S. PATENT DOCUMENTS

| | | | | |
|---|---|---|---|---|
| 4,335,300 A | * | 6/1982 | Shepherd | G06C 1/00 235/123 |
| 2003/0091687 A1 | * | 5/2003 | Copelan | A23L 33/30 426/2 |
| 2012/0031805 A1 | * | 2/2012 | Stolarczyk | A47J 39/006 206/541 |
| 2015/0305526 A1 | * | 10/2015 | Dietrich | A47G 19/06 220/575 |

FOREIGN PATENT DOCUMENTS

WO WO-2015170244 A1 * 11/2015 ............. A47G 21/02

* cited by examiner

*Primary Examiner* — Nguyen Q. Ha
(74) *Attorney, Agent, or Firm* — Armstrong Teasdale LLP

(57) ABSTRACT

A system for quantifying calorie values for a plurality of different caloric food categories includes a plurality of scoops. Each scoop of the plurality of scoops includes a scoop body having a respective internal volume and a first visual indicator. The system also includes a reference guide having a second visual indicator configured such that an association of the first visual indicator with the second visual indicator matches a first caloric food category of the plurality of different food caloric categories with a first one of the plurality of scoops, where at least one of the first visual indicator and the second visual indicator represents an amount of calories of the first caloric food category contained in the respective internal volume when substantially filled with the first caloric food category.

33 Claims, 6 Drawing Sheets

SYSTEMS AND METHODS FOR QUANTIFYING CALORIE VALUES FOR A PLURALITY OF DIFFERENT CALORIC FOOD CATEGORIES

CROSS-REFERENCE TO RELATED APPLICATIONS

This application is a National Stage of International Application No. PCT/US2016/041869, filed Jul. 12, 2016.

BACKGROUND

The field of the disclosure relates generally to a containment apparatus for food consumption, preparation, service, and packaging, and, more specifically, to systems and methods for dispensing and quantifying calorie values consumed of foods belonging to a plurality of different caloric food categories.

Individuals often desire to quantify and control the number of calories of food consumed over a specific period of time. Control, however, of food caloric intake is challenging to undertake for extended periods, and individuals' personal dietary goals are as varied as their tastes in food. A wide variety of supportive tools are available for this purpose. For example, the United States Department of Agriculture (USDA) publishes dietary guidance for a recommended daily food intake for individuals based on factors such as age and physical activity level. At least some known systems and methods for quantifying food caloric intake use recommendations such as from the USDA as a baseline and adjust the recommended daily food intake up or down based on an individual's desired goals. The USDA and similar bodies compile data including calories per volume of commonly consumed foods and drinks (e.g., the USDA's "Nutritive Value of Foods" publication).

At least some known systems for quantifying food caloric intake utilize calories per volume schemes for common or custom-prepared foods, but food items in these conventional systems are categorized primarily based upon food groups (i.e., grains, meats, etc.). These systems also typically require consumers to maintain a calorie count throughout, for example, the course of a day, and often bind the consumer to specific recipes and dishes selected from a limited variety of food items. Moreover, consumers of these conventional systems often must pay substantially more for custom-prepared and pre-packaged foods that are sold as a part of a wider system for, especially, weight loss (i.e., dieting) applications.

Further, at least some known systems quantify caloric intake based only on commonly used volumes (e.g., calories per cup, pint, quart, etc.), or by a "points" scheme. These common-volumes and points systems are burdensome to the consumer by requiring significant mathematical conversions to determine the actual caloric intake of a meal, and are thus a source of frustration that often leads to failure of the consumer easily monitoring his or her intake.

Conventional calorie counting systems are also typically restricted to one particular dietary goal, such as weight loss or maintenance, a sports nutrition purpose, or restrictions due to dietary limitations (e.g., low-sodium, gluten-free, dairy-free, etc.). These conventional systems, however, are not versatile to serve different dietary goals or preferences. These conventional systems also often require utilizing numerous volumetric measuring devices and/or kitchen scales when preparing foods, and tools such as logs and calculators to then track the calories consumed. Some consumers (e.g., people having certain medical conditions and their caregivers) may also be concerned with what proportion of their dietary caloric intake comes from certain classes of nutrients (e.g., sugars, fats, and cholesterols), and find such tracking and logging to be cumbersome and difficult to adhere to effectively on a routine and sustainable basis. Even where such consumers are not relying on costly conventional pre-packaged food items, there are still a multitude of manual steps and mathematical calculations involved that, even with the aid of a number of known smartphone "apps" and similar software applications, are time-consuming and unduly complicated.

Another known drawback of conventional caloric quantification systems is that they cannot easily and effectively be utilized in settings outside the home of the consumer. Thus, there is a need for a more standardized system and method for consumers to regularly and effectively use in all environments where they are likely to consume, serve, purchase, and prepare foods of all types, no matter what their particular tastes and preferences.

Known systems and methods for quantifying food caloric intake also do not enable users to track food caloric intake without undue complexity (e.g., using multiple smartphone apps and/or numerous measuring devices), and complicated and time-consuming manual tasks like researching foods and performing numerous mathematical calculations. Such excessively burdensome steps lead to high rates of frustration and stress among users of known systems and methods for quantifying food caloric intake which may cause users not to reach their specific personal dietary goals. Thus, there is a need for an improved system and method for quantifying food caloric intake which categorizes all food items in a more simplified, cost-effective, and manageable manner that does not require users to perform excessive mathematical calculations, can be used with a single reference guide including an app, which is applicable and efficacious in any context where foods are consumed, prepared, served, packaged, and sold, and which improves the likelihood of success in meeting personal dietary goals.

SUMMARY

Systems and methods according to the present Application present straightforward and manageable ways for a consumer to count and track food calories consumed in simple round numbers that are easy for the consumer to mentally track without the use of calculating tools or devices, and according to the consumer's choice of food items and categories. The novel and advantageous systems and methods described herein enable consumers to easily monitor their caloric intake over the course of a day, or meal, with significantly fewer restrictions and limitations experienced as compared with conventional systems, and also at a greatly reduced cost. The systems and methods of the present Application are equally versatile for all types of dietary needs or goals, and can be more easily implemented outside of the consumer's home, and in a wide variety of contexts where foods are prepared, served, consumed, and purchased.

In one aspect, a system for quantifying calorie values for a plurality of different caloric food categories is provided. The system includes a plurality of scoops. Each scoop of the plurality of scoops includes a scoop body having a respective internal volume and a first visual indicator. The system also includes a reference guide having a second visual indicator configured such that an association of the first visual indicator with the second visual indicator matches a first caloric food category of the plurality of different caloric food categories with a first one of the plurality of scoops, where at least one of the first visual indicator and the second visual indicator represents an amount of calories of the first caloric food category contained in the respective internal volume when substantially filled with the first caloric food category.

In another aspect, a method for quantifying food calorie values for a plurality of different caloric food categories is provided. Each caloric food category of the plurality of different caloric food categories is categorized based on a volumetric calorie density of at least one food item belonging to a respective caloric food category of the plurality of different caloric food categories. The method includes selecting a particular one scoop from a plurality of scoops, each scoop of the plurality of scoops having a first visual indicator and a respective internal volume. The method also includes matching the first visual indicator with a reference guide including a second visual indicator configured such that an association of the first visual indicator with the second visual indicator matches a first caloric food category of the plurality of different caloric food categories with a first one scoop of the plurality of scoops, where at least one of the first visual indicator and the second visual indicator represents an amount of calories of the first caloric food category contained in the respective internal volume when substantially filled with the first caloric food category. The method further includes transferring, using the one scoop, the respective internal volume of at least one food item belonging to the first caloric food category to at least one of a consumption, preparation, service, packaging, display, transport, sale, and storage location.

In yet another aspect, a system for quantifying nutritive element values for a plurality of different food nutrient categories is provided. Each food nutrient category of the plurality of different food nutrient categories is categorized based on a volumetric density of a respective nutritive element of at least one food item belonging to a respective food nutrient category of the plurality of different food nutrient categories. The system includes a plurality of scoops. Each scoop of the plurality of scoops includes a scoop body having a respective internal volume and a first visual indicator. The system also includes a reference guide having a second visual indicator configured such that an association of the first visual indicator with the second visual indicator matches a first food nutrient category of the plurality of different food nutrient categories with a first one of the plurality of scoops. At least one of the first visual indicator and the second visual indicator represents an amount of the respective nutritive element of the first food nutrient category contained in the respective internal volume when substantially filled with the first food nutrient category, where the respective nutritive element is one of sugar, fat, cholesterol, fiber, protein, and glycemic index.

DRAWINGS

These and other features, aspects, and advantages of the present disclosure will become better understood when the following detailed description is read with reference to the accompanying drawings in which like characters represent like parts throughout the drawings, wherein.

Figure 1:
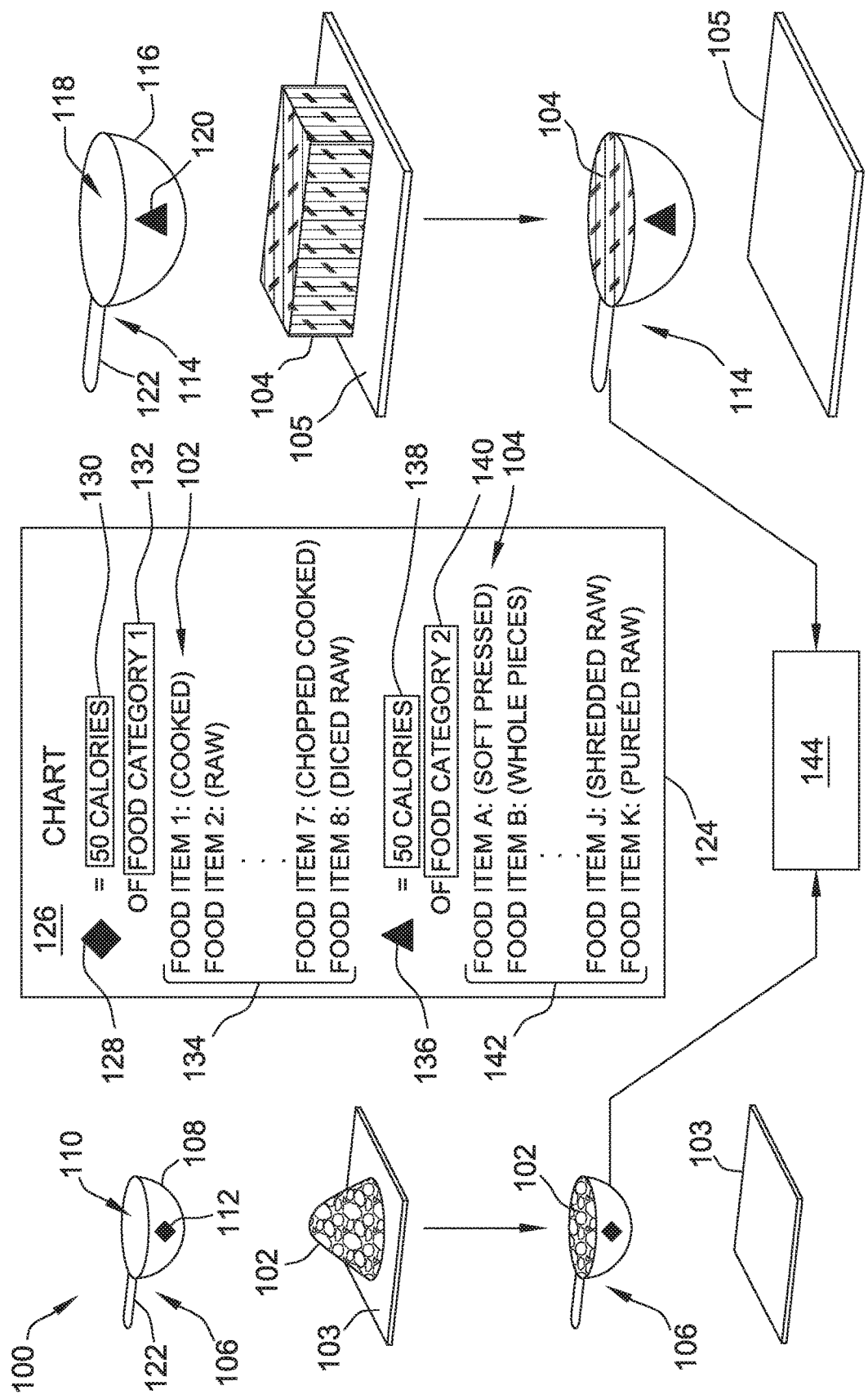
FIG. 1 is a diagram of an exemplary system for quantifying calorie values for a plurality of different caloric food categories.

Unless otherwise indicated, the drawings provided herein are meant to illustrate features of embodiments of this disclosure. These features are believed to be applicable in a wide variety of systems comprising one or more embodiments of this disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged, and such ranges are identified and include all the sub-ranges contained therein unless context or language indicates otherwise.

As used herein, the terms "processor" and "computer" and related terms, e.g., "processing device", "computing device", and "controller", are not limited to just those integrated circuits referred to in the art as a computer, but broadly refers to a microcontroller, a microcomputer, a programmable logic controller (PLC), an application specific integrated circuit (ASIC), and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner.

Furthermore, in an exemplary embodiment, additional output channels may include, but not be limited to, an operator interface monitor.

Furthermore, as used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

The systems and methods for quantifying calorie values consumed of foods belonging to a plurality of different caloric food categories described herein provide a more effective, less challenging, and less frustrating tool for people to control and quantify food caloric intake to achieve personal dietary goals over extended periods of time with a higher probability of success relative to known systems and methods. The embodiments described herein also facilitate categorization of a wide variety of food items based on volumetric calorie density rather than merely based on food groups. The embodiments described herein are further suited to providing greater selection of food items for use in a regimented, yet simplified dietary regime. The systems and methods for quantifying calorie values consumed of foods belonging to a plurality of different caloric food categories described herein are also suited to enabling a more cost-effective, less complex, and less time-consuming tool to achieve personal dietary goals of any type. The embodiments described herein are further suited to providing more accurate logging, counting, and tracking of food calories consumed over periods of time using a more uniform and standardized set of equipment implementable in any environment where foods are prepared, packaged, served, consumed, sold, and purchased.

FIG. 1 is a diagram of an exemplary system 100 for quantifying calorie values for a plurality of different caloric food categories. In an exemplary embodiment, each caloric food category of the plurality of different caloric food categories includes at least one food item (e.g., a first food item 102 situated on a first surface 103, and a second food item 104 situated on a second surface 105). System 100 includes a plurality of scoops including a first scoop 106 with a first scoop body 108 having a first internal volume 110. First scoop 106 also includes a first visual indicator (VI) 112 of a first type (e.g., a diamond shape). The plurality of scoops also includes a second scoop 114 with a second scoop body 116 having a second internal volume 118. Second scoop 114 also includes a second-type first VI 120 (e.g., a triangle shape) different from first-type first VI 112. Also, in an exemplary embodiment, the plurality of scoops in system 100 are embodied by at least two separate scoops (e.g., first scoop 106 and second scoop 114) having at least two separate and distinct scoop bodies (e.g., first scoop body 108 and second scoop body 116). A handle 122 is optionally coupled to first scoop body 108 and optionally coupled to second scoop body 116. In other embodiments, not shown, at least one of first scoop body 108 and second scoop body 116 does not include handle 122 coupled thereto. In still other embodiments, not shown, handle 122 is detachably coupled to at least one of first scoop body 108 and second scoop body 116.

First-type first VI 112 and second-type first VI 120 are at least one of printed, painted, molded, applied (e.g., as a sticker), and otherwise formed and positioned at least one of during and after manufacture of first scoop 106 and second scoop 114, respectively. In an exemplary embodiment, first-type first VI 112 and second-type first VI 120 are positioned on exterior surfaces of first scoop body 108 and second scoop body 116, respectively. In other embodiments, not shown, first-type first VI 112 and second-type first VI 120 are positioned on handle 122 of first scoop 106 and positioned on handle 122 second scoop 114, respectively. In still other embodiments, not shown, first-type first VI 112 is positioned on handle 122 of first scoop 106 and second-type first VI 120 is positioned on second scoop body 116 of second scoop 114 (e.g., where a size of first scoop body 108, and thus first internal volume 110, is not sufficient to clearly and effectively position first-type first VI 112 on first scoop body 108). In yet other embodiments, not shown, at least one of first-type first VI 112 and second-type first VI 120 are at least one of removable, detachable, editable, reusable, and replaceable from first scoop 106 and second scoop 114, respectively.

A material of construction of each scoop of the plurality of scoops of system 100 includes suitable materials that are safe for use in applications where the particular material chosen shall be in regular contact with various foods (in both liquid and solid states) intended for human consumption in a wide variety of forms and states (e.g., "food grade" materials including, without limitation, various plastics, glasses, woods, and metals). Some such food grade materials of construction include materials that facilitate washing and reusing at least one scoop of the plurality of scoops in system 100, while other food grade materials may not be amenable to repeated washing and reuse, and are better suited to single- or limited-use disposable embodiments of at least one scoop of the plurality of scoops in system 100.

System 100 also includes a reference guide 124. In an exemplary embodiment, reference guide 124 is embodied by a chart 126. Chart 126 includes a plurality of second VIs including a first-type second VI 128 (e.g., a diamond shape) matching first-type first VI 112. Chart 126 also includes a first number of calories 130 of a first caloric food category 132 (i.e., to which first food item 102 belongs) contained in first internal volume 110 when first scoop body 108 is substantially filled with first food item 102 and/or other food items belonging to first food category 132. Chart 126 further includes an indication of the identity of first caloric food category 132 along with a first listing of food items 134 belonging thereto. Similarly, in an exemplary embodiment, the plurality of second VIs also includes a second-type second VI 136 (e.g., a triangle shape) matching second-type first VI 120. Likewise, chart 126 includes a second number of calories 138 of a second caloric food category 140 (i.e., to which second food item 104 belongs) contained in second internal volume 118 when second scoop body 116 is substantially filled with second food item 104 and/or other food items belonging to second caloric food category 140. Chart 126 further includes an indication of the identity of second caloric food category 140 along with a second listing of food items 142 belonging thereto. Also, in an exemplary embodiment, first number of calories 130 and second number of calories 138 are denoted on chart 126 as numerical values (e.g., "50 Calories") representative of the number of kilocalories (kcal, also referred to as Calories (Cal) and "large calories", and the most common unit of food energy content used in the United States, e.g., on food labels). In other embodiments, not shown, first number of calories 130 and second number of calories 138 are denoted on chart 126 as numerical values alone without the corresponding food energy unit included, and the specific units represented numerical values alone are included elsewhere on at least one of reference guide 124, a packaging of system 100, the plurality of scoops, and user instructions for system 100.

In an exemplary embodiment, at least one of first-type first VI 112 and second-type first VI 120 includes at least one of a color (i.e., of at least one of first scoop body 108, second scoop body 116, and at least one handle 122 thereof), a graphic symbol or pattern, a shape defined by at least one of first scoop body 108, second scoop body 116, and at least one handle 122 thereof, and an alphanumeric symbol including at least one of a letter, a number, and a word. Also, in an exemplary embodiment, first-type first VI 112 and second-type first VI 120 are identical to first-type second VI 128 and second-type second VI 136, respectively. In other embodiments, not shown, at least one of first-type first VI 112 and second-type first VI 120 is not identical to at least one of first-type second VI 128 and second-type second VI 136, respectively. For example, and without limitation, in other embodiments, not shown, first-type first VI is embodied by a square shape having a color (e.g., green) and first-type second VI 128 is embodied by a visible region of reference guide 124 (e.g., at least one row of information of chart 126) having a matching color (e.g., green), but not including the square shape. In this example, a user of system 100 is enabled to associate and match first-type first VI 112 with first-type second VI 128 despite the two VIs not being completely identical.

Further, in an exemplary embodiment, first-type second VI 128 is located on chart 126 proximate first number of calories 130, an indication of the identity of first caloric food category 132 (e.g., "food category 1"), and first listing of food items 134. Similarly, second-type second VI 136 is located on chart 126 proximate second number of calories 138, an indication of the identity of second caloric food category 140 (e.g., "food category 2"), and second listing of food items 142. First listing of food items 134 and second listing of food items 142 includes the identities of at least one food item belonging to first caloric food category 132 and second caloric food category 140, respectively. Further, in an exemplary embodiment, each respective food item listed in first listing of food items 134 and second listing of food items 142 includes an indication of a state of preparation (e.g., raw, cooked, chopped, diced, puréed, etc.). Furthermore, in an exemplary embodiment, at least one of first-type second VI 128 and second-type second VI 136 are at least one of removable, detachable, reusable, editable, and replaceable from reference guide 124 in system 100.

For example, and without limitation (and based on information contained in Table 9 of the USDA's "Nutritive Value of Foods" publication), when first internal volume 110 is held constant, first scoop 106 substantially filled with uncooked couscous grain contains a significantly greater amount of calories than first scoop 106 substantially filled with cooked couscous grain (i.e., due to water absorbed by the grain during cooking). As a further example, finely chopped walnuts enable more closely spaced individual pieces and, thus, a greater mass of this food item and a greater amount of calories to be contained in first internal volume 110 relative to whole shelled walnuts when first scoop 106 is substantially filled. Further examples commonly encountered by users of system 100 include, without limitation, a powdered versus liquid state (e.g., milks), and "light" versus "whole" designations (e.g., yogurts). Therefore, in an exemplary embodiment, a general identity of food item (e.g., walnuts) in a single caloric food category of the plurality of different caloric food categories is not, in all cases, sufficient for a user of system 100 to fully benefit therefrom. Instead, a general food item identity designation such as simply "walnuts" is further categorized into a plurality of specific food items belonging to plurality of different caloric food categories based on, for example and without limitation, a state of preparation upon a user of system 100 filling the respective internal volume of the particular one scoop of the plurality of scoops for use with the specific food item, as further shown and described below.

Furthermore, in an exemplary embodiment, reference guide 124 is configured such that an association of the first VI (e.g., first-type first VI 112) with the second VI (e.g., first-type second VI 128) matches a respective one caloric food category (e.g., first caloric food category 132) of the plurality of different caloric food categories with a first one scoop (e.g., first scoop 106) of the plurality of scoops. When such association of first VI with second VI is made by a user of system 100, reference guide 124 is further configured to facilitate at least one of the first VI and the second VI to be representative of an amount of calories (e.g., first number of calories 130 in the case of first scoop 106) contained in the respective internal volume (e.g., first internal volume 110) when the respective scoop body (e.g., first scoop body 108) is substantially filled with a food item (e.g., first food item 102) belonging to the respective caloric food category (e.g., first caloric food category 132).

Each respective caloric food category of the plurality of different caloric food categories is categorized based on a volumetric calorie density of at least one food item belonging to the respective caloric food category. In an exemplary embodiment, each scoop of the plurality of scoops has a different respective internal volume and the amount of calories of each respective food item belonging to the respective caloric food category contained in the respective internal volume is substantially equal. For example, and without limitation, a substantially equal volume of whole milk, canned sectioned grapefruit in light syrup, and regular plain non-fortified cooked oatmeal contains a substantially equal number of calories, and thus these three food items are categorized in the same one caloric food category. Therefore, food item members of respective caloric food categories have substantially equal volumetric calorie densities despite being drawn from a variety of different food groups (e.g., dairy, fruit, and grain in the above example). Furthermore, when at least one food item is categorized into the respective caloric food category based on volumetric calorie density, the respective internal volume of the respective one scoop corresponding to the respective caloric food category is scalable to a desired multiple of the amount of calories (e.g., a round number of calories) contained in the respective internal volume. Similarly, a tolerance (e.g., ±a percentage (%) of calories per unit volume) for volumetric calorie density for a plurality of food items belonging to the respective caloric food category dictates the number of different food items that are able to be categorized into one particular caloric food category. By loosening (i.e., increasing the ±% value) the allowable tolerance for volumetric calorie density for the respective caloric food category, a greater number of food items are able to be categorized therein.

For example, and without limitation, the amount of calories of the at least one food item belonging to a respective caloric food category of the plurality of different caloric food categories contained in the respective internal volume is within a predetermined range of a round number of calories. In an exemplary embodiment, first internal volume 110 of first scoop body 108 is configured to contain first number of calories 130 of first food item 102, and first number of calories 130 is 50 calories (i.e., 50 kcal). Similarly, second internal volume 118 of second scoop body 116 is configured to contain second number of calories 138 of second food item 104, and second number of calories 138 is also 50 calories (i.e., 50 kcal). In an exemplary embodiment, first internal volume 110 is further configured to contain 50 calories of first food item 102, along with at least one additional food item (e.g., "food item 2" in FIG. 1) belonging to first caloric food category 132 by virtue of it having a volumetric calorie density substantially equal to first food item 102. Similarly, second internal volume 118 is further configured to contain 50 calories of second food item 104, along with at least one additional food item (e.g., "food item B" in FIG. 1) belonging to second caloric food category 140 by virtue of it having a volumetric calorie density substantially equal to second food item 104. Thus, in an exemplary embodiment, filling first scoop body 108 with at least one of one food item belonging to first caloric food category 132 and a plurality of different food items which all belong to first caloric food category 132 results in 50 calories of food contained in first internal volume 110. Likewise, filling second scoop body 116 with at least one of one food item belonging to second caloric food category 140 and a plurality of different food items which all belong to second caloric food category 140 results in 50 calories of food contained in second internal volume 118.

In an exemplary embodiment, first number of calories 130 and second number of calories 138 are both a round number of calories (e.g., 50 kcal). The round number of calories (e.g., 50 kcal) is both an integer multiple of 10 and an integer multiple of 5. Using round numbers for first number of calories 130 and second number of calories 138 is convenient for users of system 100 to at least one of count, keep track of, and record total numbers of calories transferred from at least one respective scoop of the plurality of scoops to a location 144 including, for example and without limitation, at least one of a consumption, preparation, service, packaging, display, transport, sale, and storage location. In other embodiments, not shown, the round number of calories contained in at least one of first internal volume 110 and second internal volume 118 is an integer multiple of 5, but not also an integer multiple of 10 (e.g., 25 kcal).

Also, in an exemplary embodiment, the tolerance (i.e., ±%) for the amount of calories of each food item belonging to a respective caloric food category of the plurality of different caloric food categories contained in a respective internal volume is within a predetermined percentage of the respective round number of calories. Further, in an exemplary embodiment, the round number of calories (e.g., 50 kcal) contained in first internal volume 110 is substantially equal to the round number of calories (e.g., 50 kcal) contained in second internal volume 118. In other embodiments, not shown, first internal volume 110 is configured to contain a first round number of calories (e.g., 50 kcal) different from a second round number of calories (e.g., 100 kcal) for second internal volume 118. Furthermore, in an exemplary embodiment, first internal volume 110 is defined by a volume of first scoop body 108 that is substantially different in value that second internal volume 118 of second scoop body 116. For example, and without limitation, where food items belonging to first caloric food category 132 have greater volumetric calorie densities than food items belonging to second caloric food category 140, containing 50 kcal in first internal volume 110 requires a lesser volume than does containing 50 kcal in second internal volume 118.

Further, in an exemplary embodiment, the predetermined percentage of the respective round number of calories is >5% and ≤10% for each caloric food category of the plurality of different caloric food categories. For example, and without limitation, where each respective internal volume of the plurality of scoops in system 100 is configured to contain 50 kcal as the round number of calories, an amount of calories of the at least one respective food item belonging to the respective caloric food category matched to the respective scoop and contained in the respective internal volume when substantially filled is 45-55 kcal. Similarly, for example, where first internal volume 110 of first scoop body 108 is configured to contain 100 kcal (i.e., first number of calories 130) of at least first food item 102 and second internal volume 118 is configured to contain 25 kcal (i.e., second number of calories 138), first internal volume 110 will actually contain 90-110 kcal of at least one first food item 102 and second internal volume 118 will actually contain 22.5-27.5 kcal of at least one second food item 104.

In other embodiments, the predetermined percentage of the respective round number of calories for at least one caloric food category of the plurality of different caloric food categories is at least one of <2%, >2% and ≤5%, >10% and ≤15%, and >15% and ≤25%. Clearly, then, as the predetermined percentage (i.e., ±% tolerance) of the respective round number of calories for a respective caloric food category increases, the number of food items belonging to the respective caloric food category increases. For example, and without limitation, caloric food categories having a predetermined percentage of the respective round number of calories ≤5% enables users of system 100 to maintain tighter control over their consumption of certain food items. A user of system 100 such as one who has allergies and/or adverse reactions (e.g., peanut allergy and lactose intolerance) and who experiences such adverse events if they consume in excess of a known amount of calories of those known food items benefits from system 100 having such lower predetermined percentages (i.e., tolerances). Similarly, certain users of system 100 (e.g., persons having diabetic and hypercholesterolemia conditions) also benefit from tighter tolerances where they know that certain food item(s) contain a known quantity of calories from specific nutritive elements (e.g., sugars and cholesterol) as part of the respective round number of calories. Likewise, system 100 benefits users such as patients and caregivers in medical, nursing, and similar contexts where tighter tolerances and more specific quantification of food calorie intake including, without limitation, calories from specific nutritive elements, is important. On the other hand, users of system 100 who are interested in quantification of food caloric intake for purposes of weight gain (e.g., bodybuilders and persons suffering or recovering from certain degenerative diseases) need not employ system 100 with a tight tolerance such as ≤5%, and benefit from the greater number of food items belonging to respective caloric food categories with looser tolerances (e.g., >10%). Also, a user of system 100 who desires to at least one of lose weight in a healthy manner, maintain a healthy weight, and quantify, record, and track total food calorie consumption over finite periods of time (e.g., 1900 to 2100 calories per day), including, without limitation, from among at least one food group, benefits from a medium tolerance (e.g., 5-10%) for the predetermined percentage of the respective round number of calories.

Furthermore, in an exemplary embodiment, at least one of first listing of food items 134 and second listing of food items 142 includes nutrient content information (not shown in FIG. 1) for at least one food item belonging to the respective caloric food category. For example, and without limitation, nutrient content information includes at least one of a number of calories and a percentage of a total amount of calories contained in the respective internal volume from at least one of fat, carbohydrate, fiber, and protein. In other embodiments, not shown, the nutrient content information is listed on a separate chart which is at least one of detached from and on a reverse side of chart 126. In still other embodiments, not shown, reference guide 124 is embodied by a printed book, and in yet other embodiments, reference guide 124 is embodied by an electronic reference guide including, without limitation, a computer display-viewable file (e.g., portable document format (pdf)), an e-book, and a mobile application (i.e., "app") such as executable by mobile communications devices such as smart phones, tablet computers, and laptop computers.

Figure 2:
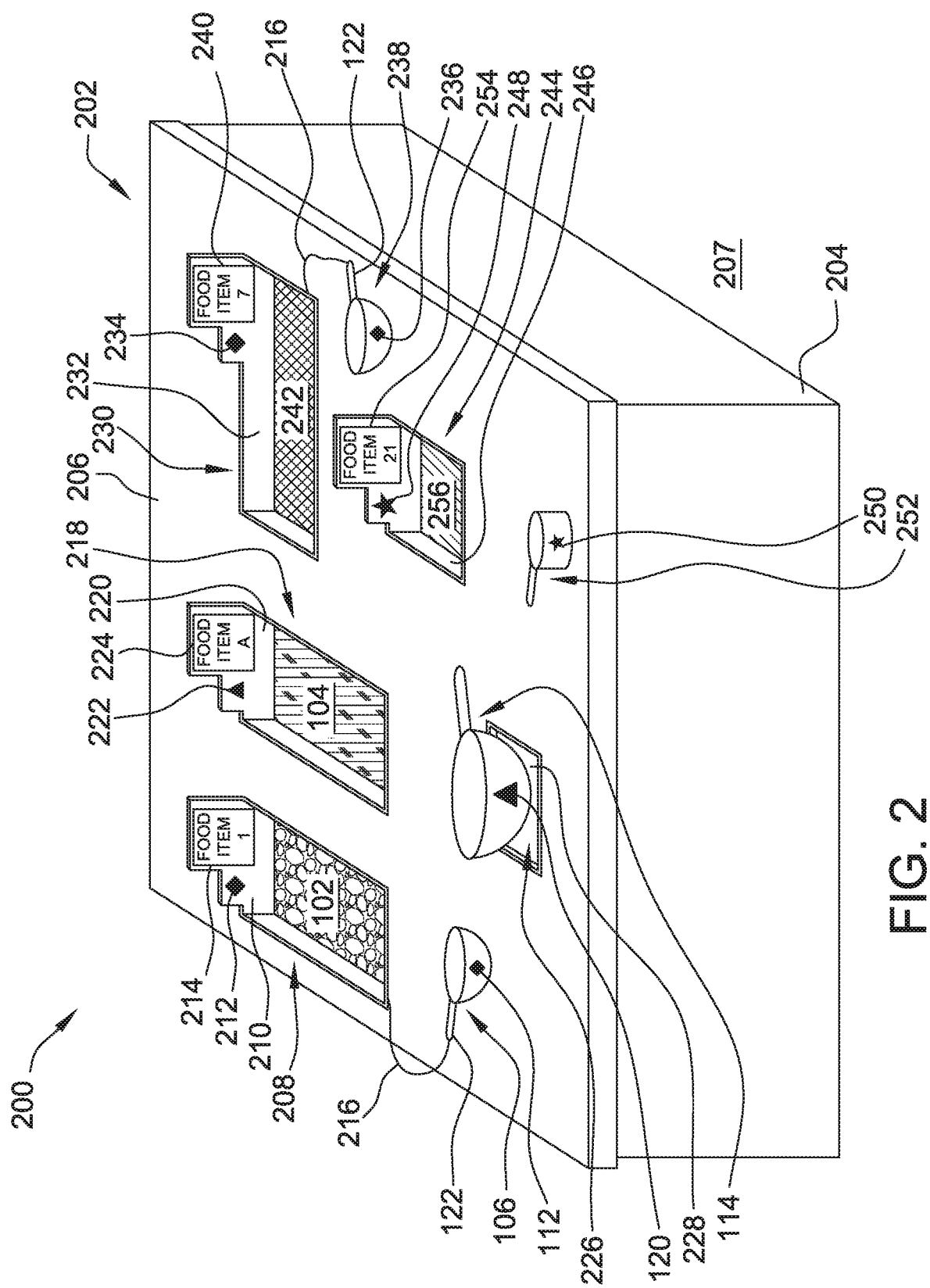
FIG. 2 is a diagram of an exemplary food service system that may be used with the system shown in FIG. 1.

FIG. 2 is a diagram of an exemplary embodiment of a food service system 200 that may be used with system 100 shown in FIG. 1. In an exemplary embodiment, food service system 200 includes a food display assembly 202. Also, in an exemplary embodiment, food service system 200 is embodied by, for example and without limitation, at least one of a salad bar and a buffet-style food bar. Food display assembly 202 includes at least one supportive member (e.g., a stand 204), and a surface (e.g., a tabletop 206) positioned atop stand 204 and supported thereby above a walking surface (e.g., a floor 207). Tabletop 206 surface, in an exemplary embodiment, is embodied by a substantially flat planar surface to facilitate cleaning thereof. Further, in an exemplary embodiment, food service system 200 includes a plurality of food containers positioned at least one of upon and at least partially through tabletop 206, such that the plurality of containers are viewable from floor 207 by a user of food service system 200. Each food container of the plurality of food containers is configured to contain at least one respective food item belonging to at least one respective caloric food category of the plurality of different caloric food categories. The plurality of food containers includes a first food container 208 including a first container body 210 and a third VI 212 of a first type (e.g., a diamond shape) identical to first-type first VI 112 of first scoop 106. First food container 208 also includes a first-type fourth VI 214. Similar to first and second VIs as described above with reference to FIG. 1, at least one of first-type fourth VI 214, as well as second, third, etc. fourth VIs shown and described below, includes at least one of a color (i.e., of at least a portion of at least one of food container of the plurality of food containers), at least one of a graphic symbol and a pattern affixed to a respective food container, a shape (i.e., design) defined by at least one of food container of the plurality of food containers, and an alphanumeric symbol including at least one of a letter, a number, and a word.

Also, in an exemplary embodiment, first food container 208 contains first food item 102 of first caloric food category 132. First-type third VI 212 is configured to indicate the amount of calories (e.g., first number of calories 130) of first food item 102 contained in first internal volume 110 of first scoop 106, as further shown and described above with reference to FIG. 1. Thus, first-type third VI 212, as well as second, third, etc. third VIs shown and described below, facilitate users of system 100 and food service system 200 to match a respective scoop of the plurality of scoops in system 100 to at least one food container of the plurality of food containers in food service system 200. Similar to first and second VIs as described above with reference to FIG. 1, at least one of first-type third VI 212, as well as second, third, etc. third VIs shown and described below, includes at least one of a color (i.e., of at least a portion of at least one of food container of the plurality of food containers), at least one of a graphic symbol and a pattern affixed to a respective food container, a shape (i.e., design) defined by at least one of food container of the plurality of food containers, and an alphanumeric symbol including at least one of a letter, a number, and a word.

Further, in an exemplary embodiment, first-type fourth VI 214 is configured to indicate an identity of the at least one respective food item (e.g., first food item 102 identified as "Food Item 1") contained in first food container 208. For example, and without limitation, first food container 208 is further configured to contain at least one prepared food item (e.g., a first food item 102 embodied by a cooked "food item 1") belonging to first caloric food category 132, where the amount of calories (e.g., first number of calories 130) is representative of an amount of calories of the at least one first food item 102 in a prepared (i.e., ready to eat) state. Furthermore, in an exemplary embodiment, at least one scoop (e.g., handle 122 of first scoop 106) of the plurality of scoops is optionally coupled through a link 216 (e.g., a flexible, durable, and sanitary cable) to at least one food container (e.g., first food container 208) of the plurality of food containers. Moreover, in an exemplary embodiment, link 216 is coupled to and between first food container 208 and handle 122 of first scoop 106. In other embodiments, not shown, first scoop 106 is coupled through link 216 to at least one of tabletop 206 and stand 204. In yet other embodiments, not shown, link 216 is coupled to first scoop body 108 rather than to handle 122.

Furthermore, in an exemplary embodiment, the plurality of food containers of food service system 200 includes a second food container 218 including a second container body 220 and a second-type third VI 222 (e.g., a triangle shape) identical to second-type first VI 120 of second scoop 114. Second food container 218 also includes a second-type fourth VI 224. Further, in an exemplary embodiment, second food container 218 contains second food item 104 of second caloric food category 140. Second-type third VI 222 is configured to indicate the amount of calories (e.g., second number of calories 138) of second food item 104 contained in second internal volume 118 of second scoop 114, as further shown and described above with reference to FIG. 1. Moreover, in an exemplary embodiment, second-type fourth VI 224 is configured to indicate an identity of the at least one respective food item (e.g., second food item 104 identified as "Food Item A") contained in second food container 218. For example, and without limitation, second food container 218 is further configured to contain at least one prepared food item (e.g., a second food item 104 embodied by a soft pressed "food item A") belonging to second caloric food category 140, where the amount of calories (e.g., second number of calories 138) is representative of an amount of calories of the at least one second food item 102 in the prepared state. Also, in an exemplary embodiment, food display assembly 202 includes at least one scoop receptacle 226 formed as a suitably-shaped recessed surface 228 in at least one partial area of tabletop 206 surface area. Similar to a function served by link 216, scoop receptacle 226 is configured to restrict an extent of user-initiated movement of second scoop 114 to, for example and without limitation, ensure that second scoop 114 remains in a location proximate second food container 218 when not in use therewith in food service system 200.

Moreover, in an exemplary embodiment, the plurality of food containers of food service system 200 includes a third food container 230 including a third container body 232 and a third-type third VI 234 (e.g., a diamond shape) identical to a third-type first VI 236 of a third scoop 238. Third food container 230 also includes a third-type fourth VI 240. Moreover, in an exemplary embodiment, third food container 230 contains a third food item 242 of a third caloric food category of the plurality of different caloric food categories. Third-type third VI 234 is configured to indicate the amount of calories (e.g., a third number of calories) of third food item 242 contained in a third internal volume of third scoop 238. Also, in an exemplary embodiment, third-type fourth VI 240 is configured to indicate an identity of at least one respective food item (e.g., third food item 242 identified as "Food Item 7") contained in third food container 230. Also, in an exemplary embodiment, the plurality of food containers of food service system 200 includes a fourth food container 244 including a fourth container body 246 and a fourth-type third VI 248 (e.g., a star shape) identical to a fourth-type first VI 250 of a fourth scoop 252. Fourth food container 244 also includes a fourth-type fourth VI 254. Further, in an exemplary embodiment, fourth food container 244 contains a fourth food item 256 of a fourth caloric food category of the plurality of different caloric food categories. Fourth-type third VI 254 is configured to indicate the amount of calories (e.g., a fourth number of calories) of fourth food item 256 contained in a fourth internal volume of fourth scoop 252. Further, in an exemplary embodiment, fourth-type fourth VI 254 is configured to indicate an identity of at least one respective food item (e.g., fourth food item 256 identified as "Food Item 21") contained in fourth food container 244.

Also, in an exemplary embodiment, at least one of first-type third VI 212, second-type third VI 222, third-type third VI 234, and fourth-type third VI 248 is at least one of removable, detachable, editable, reusable, and replaceable from at least one food container of the plurality of food containers of food service system 200. At least one of first-type fourth VI 214, second-type fourth VI 224, third-type fourth VI 240, and fourth-type fourth VI 254 is also at least one of removable, detachable, editable, reusable, and replaceable from at least one food container of the plurality of food containers of food service system 200. Also, as shown and described above with reference to FIG. 1, a material of construction of each container of the plurality of containers of food service system 200 includes suitable materials that are safe for use in applications where the particular material chosen shall be in regular contact with various foods intended for human consumption in a wide variety of forms and states (e.g., "food grade" materials including, without limitation, various plastics, glasses, woods, and metals). Such materials include, without limitation, materials that facilitate washing and reusing at least one container of the plurality of containers in food service system 200, while other food grade materials may not be amenable to repeated washing and reuse, and are better suited to single-use disposable embodiments of at least one container of the plurality of containers in food service system 200.

Figure 3:
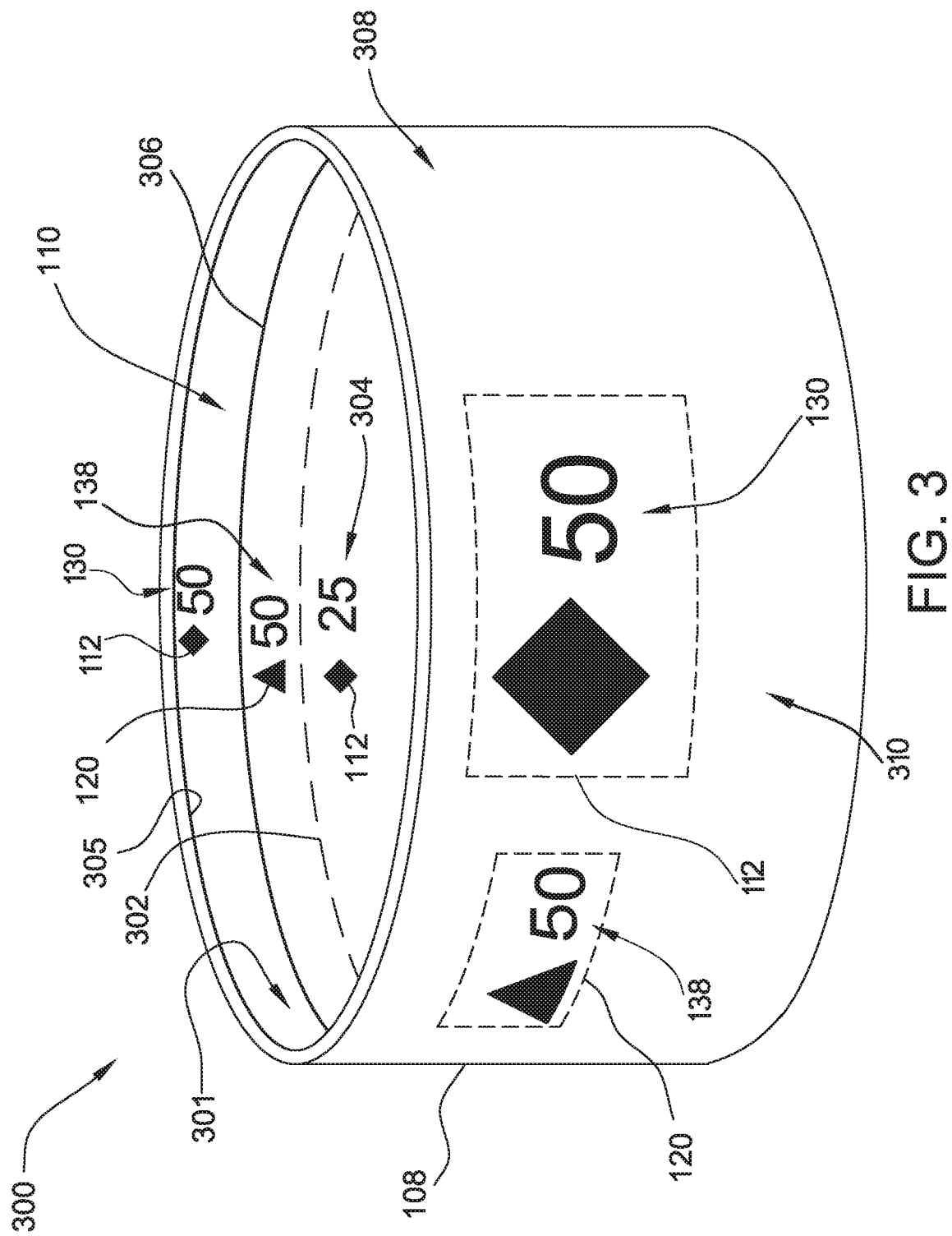
FIG. 3 is a diagram of an exemplary scoop that may be used with the systems shown in FIGS. 1 and 2.

FIG. 3 is a diagram of an exemplary scoop 300 that may be used with systems 100 and 200 shown in FIGS. 1 and 2, respectively. In this exemplary embodiment, scoop 300 is embodied by first scoop 106 including first scoop body 108 having first internal volume 110 and first-type first VI 112, as shown and described above with reference to FIG. 1. First-type first VI 112 includes first number of calories 130 (e.g., "50" to denote that first internal volume 110 contains 50 kcal as first round number of calories when substantially filled with at least first food item 102 of first caloric food category 132). In other embodiments, first-type first VI 112 including first number of calories 130 is included on at least one of first scoop body 108 and handle 122 (not shown). Further, in this exemplary embodiment, an interior food contact surface 301 of first scoop body 108 includes at least one mark (e.g., a mark 302, denoted as a dashed line in FIG. 3) configured to indicate to a user of system 100 at least one fractional value of first amount of calories (i.e., first number of calories 130) when first scoop body 108 is filled with first food item 102, not shown, to a volume substantially equal to the level indicated by mark 302.

Also, in this exemplary embodiment, first scoop body 108 includes at least one fractional calorie value indicator (e.g., a first fractional calorie value indicator 304 denoted as "25" in FIG. 3) on interior food contact surface 301 proximate mark 302. First fractional calorie value indicator 304 is configured to indicate to a user of system 100 a fractional round number of calories of first food item 102 corresponding to a state of use where first scoop body 108 is filled to a fractional value of first internal volume 110 corresponding to mark 302. Further, in this exemplary embodiment, first internal volume 110 (i.e., corresponding to first number calories 130) is marked on interior food contact surface 301 by a first graduation 305 (denoted by a first solid line in FIG. 3) included on interior food contact surface 301. First graduation 305 includes first-type first VI 112 and first number of calories 130 positioned proximate first graduation 305. Similarly, mark 302 includes first-type first VI 112 and first fractional calorie value indicator 304 positioned proximate mark 302. For example, and without limitation, filling first scoop body 108 with first food item 102 to first graduation 305 results in 50 kcal of first food item 102 contained in first scoop 106, and filling first scoop body 108 with first food item 102 to mark 302 results in 25 kcal of first food item 102 contained in first scoop 106.

In an alternative embodiment, at least one scoop 300 of the plurality of scoops in system 100 can serve as a multiple food category scoop including a plurality of VIs (e.g., first-type first VI 112 and second-type first VI 120) positioned thereupon. In this alternative embodiment, at least one scoop 300 of the plurality of scoops in system 100 is embodied by a scoop 300 having a single integral scoop body (e.g., a single scoop body including, in a single structure, the functionality of a plurality of scoops 300 including both of first scoop 106 and second scoop 114). In addition to first-type first VI 112 and first number of calories 130, in this alternative embodiment, the single integral scoop body of scoop 300 includes second-type first VI 120, along with second number of calories 138 (e.g., "50") positioned proximate second-type first VI 120.

In such multiple food category scoop embodiments having the single integral scoop body, at least two graduations are included on interior food contact surface 301. Interior food contact surface 301 of first scoop body 108 includes a second graduation 306 (denoted by a second solid line in FIG. 3) which includes second-type first VI 120 and second number of calories 138 positioned proximate second graduation 306. Second graduation 306 is positioned on the single integral scoop body at a different location thereon from first graduation 305 (e.g., to distinguish between first internal volume 110 and second internal volume 118). In other alternative embodiments, a second mark (not shown) is included and is configured, similarly to mark 302, to indicate to a user of multiple food category scoop in system 100 at least one fractional value of second amount of calories (i.e., second number of calories 138) when first scoop body 108 is filled with second food item 104, not shown, to a volume substantially equal to the level indicated by the second mark. In such other alternative embodiments, interior food contact surface 301 also optionally includes at least two fractional calorie value indicators thereon including first fractional calorie value indicator 304 and a second fractional calorie value indicator (e.g., "25", not shown in FIG. 3) positioned proximate the second mark. Second fractional calorie value indicator is configured to indicate to a user of system 100 a fractional round number of calories of second food item 104 corresponding to a state of use where first scoop body 108 is filled to a fractional value corresponding to the second mark. For example, and without limitation, filling first scoop body 108 with second food item 104 to second graduation 306 results in 100 kcal of second food item contained in first scoop 106, and filling first scoop body 108 with second food item 104 to the second mark results in 50 kcal of second food item 104 contained in first scoop 106.

Also, in alternative embodiments of system 100 having at least one scoop 300 of the plurality of scoops embodied by at least one multiple food category scoop having a single integral scoop body, at least one of first graduation 305 and second graduation 306 is optionally embodied by variations in at least one of a color, a texture, and the like of interior food contact surface 301. Similarly, in other alternative embodiments, at least one of first graduation 305, second graduation 306, mark 302, and second mark (not shown) is optionally embodied in at least one of a scribed line (i.e., an indentation), a raised line (i.e., a ridge), and the like formed in a material of construction of the single integral scoop body including, without limitation on at least one of interior food contact surface 301 and an exterior surface 308, of the multiple food category scoop. Furthermore, a person having ordinary skill in the art shall understand that alternative embodiments (and variations thereupon) which include at least one scoop 300 of the plurality of scoops embodied by at least one multiple food category scoop having the single integral scoop body optionally includes additional graduations beyond first graduation 305 and second graduation 306 (e.g., a third graduation for a third caloric food category, a fourth graduation for a fourth caloric food category, etc.). Thus, according to the same principals shown and described above with reference to FIG. 3, the single integral scoop body of the multiple food category scoop provides benefits to users of system 100 including, without limitation, an ability to use a single scoop 300 to quantify food caloric intake for two or more caloric food categories of the plurality of different caloric food calories (i.e., by using a plurality of graduations of the single integral scoop body to distinguish between first internal volume 110, second internal volume 118, a third internal volume, etc.).

In another alternative embodiment, not shown, at least one scoop 300 of the plurality of scoops in system 100 (e.g., first scoop body 108) optionally includes at least one volume indicator indicating a value of at least a portion of first internal volume 110. Volume indicator, when present, is positioned on interior food contact surface 301 proximate a volume mark. In those alternative embodiments which include volume indicator, at least one scoop 300 of the plurality of scoops in system 100 optionally includes a fractional volume indicator indicating a fractional value of volume indicator. Fractional volume indicator is positioned on interior food contact surface 301 proximate a fractional volume mark. In still other embodiments, not shown, volume indicator and fractional volume indicator include at least one of English volumetric units such as fluid ounces and metric volumetric units such as milliliters (mL). Also, in those embodiments which include volume indicator, volume indicator is intended to enable a user of system 100 to use at least one scoop of the plurality of scoops (e.g., first scoop 106) as a volume measuring device for any liquid and solid substance. Volume indicator, however, is not intended to replace or supplant the purpose and function of first-type first VI 112 and second-type first VI 120 (as shown and described above with reference to FIG. 1) in system 100. Rather, including at least one volume indicator on at least one scoop 300 of the plurality of scoops in system 100 provides a convenient additional functionality to users of system 100, and provides benefits including, without limitation, reducing the number of devices used during the course of food preparation, packaging, storage, delivery, and consumption.

Further, in the exemplary embodiment, at least one scoop 300 of the plurality of scoops in system 100 is embodied by a drinking vessel-type scoop 300 having a substantially planar and flat bottom surface 310. A user of system 100 with at least one scoop 300 configured as a drinking vessel benefits from flat bottom surface 310 where, for example and without limitation, drinking vessel-type scoop 300 is used in situations including, without limitation, filling, transporting, consuming, transferring, and storing a liquid-type first food item 102. Similarly, a user of drinking vessel-type scoop 300 having flat bottom surface 310 benefits in applications such as in the context of food service system 200 shown and described above with reference to FIG. 2. In contexts such as food service system 200, flat bottom surface 310 of at least one scoop 300 of the plurality of scoops enable users of system 100 to place scoop 300 having flat bottom surface 310 upon substantially flat surfaces such as tables, counters, bartops, and stands for periods of time without scoop 300 being easily tipped over and its contents (whether or not such contents are in a liquid state) spilled and/or otherwise contacting surfaces other than interior food contact surface 301. Relatedly, in other embodiments, not shown, at least one scoop 300 of the plurality of scoops in system 100 includes a lid configured to detachably couple to first scoop body 108 opposite a bottom surface (e.g., flat bottom surface 310) to prevent spillage of first food item 102 during at least one of transporting and storing activities of users of system 100.

In other embodiments, not shown, a material of construction of at least a portion of first scoop body 108 is embodied by at least one of a transparent material and a translucent material, either of which facilitates a user of system 100 visualizing a state of filling of scoop 300. In such transparent or translucent embodiments of at least one scoop 300 of the plurality of scoops in system 100, at least one of first-type first VI 112, second-type first VI 120, first number of calories 130, second number of calories 138, first graduation 305, second graduation 306, mark 302, second mark, first fractional calories value indicator 304, second fractional calorie value indicator, volume mark, volume indicator, fractional volume mark, and fractional volume indicator need not be included on interior food contact surface 301, but instead is optionally positioned on exterior surface 308 of first scoop body 108.

Figure 4:
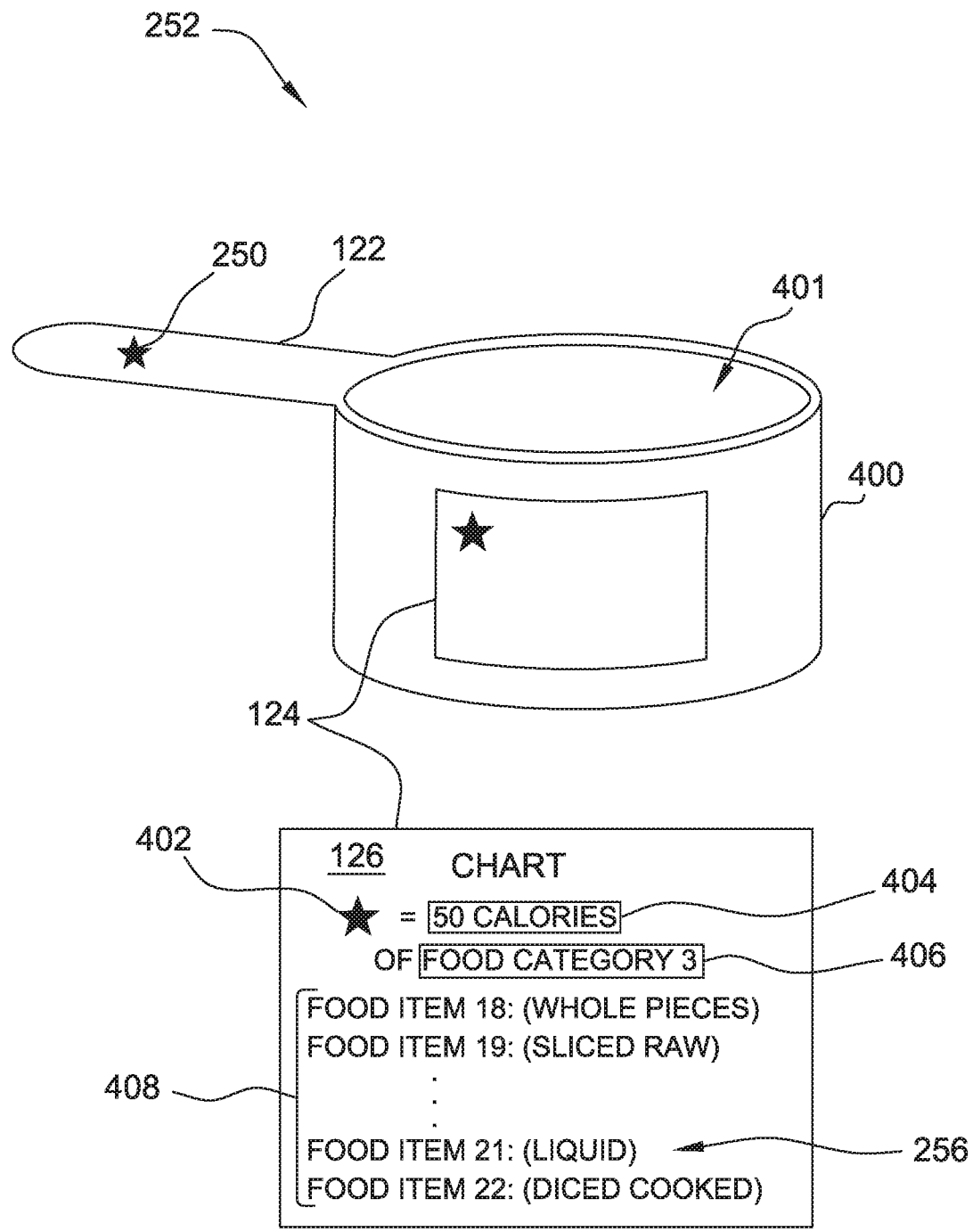
FIG. 4 is a diagram of an alternative scoop that may be used with the systems shown in FIGS. 1 and 2.

FIG. 4 is a diagram of an alternative scoop that may be used with the systems shown in FIGS. 1 and 2. In an alternative embodiment, fourth scoop 252 includes fourth-type fourth VI 250 positioned on handle 122 rather than positioned on a fourth scoop body 400. Also, in an alternative embodiment, reference guide 124 is embodied by chart 126 positioned on fourth scoop body 400. In other embodiments, not shown, reference guide 124 is positioned on handle 122 of fourth scoop 252 rather than on fourth scoop body 400. In still other embodiments, not shown, reference guide 124 is positioned on both handle 122 and fourth scoop body 400 of fourth scoop 252. Further, in an alternative embodiment, chart 126 includes a fourth-type second VI 402

(e.g., a star shape) matching fourth-type first VI 250 and fourth-type third VI 248 on fourth food container 244.

Also, in an alternative embodiment, chart 126 includes a fourth number of calories 404 (e.g., "50 calories") of a fourth caloric food category 406 (i.e., to which fourth food item 256 belongs) contained in fourth internal volume 401 when fourth scoop body 400 is substantially filled with fourth food item 256 and/or other food items belonging to fourth caloric food category 406. Further, in an alternative embodiment, chart 126 includes an indication of the identity of fourth caloric food category 406 along with a fourth listing of food items 408 belonging thereto. Furthermore, in an exemplary embodiment, chart 126 positioned upon fourth scoop 252 is embodied by a partial reference guide which includes information relevant to fourth caloric food category 406 corresponding to fourth scoop 252 only, rather than a complete reference guide 124 for system 100 as shown and described above with reference to FIG. 1.

Figure 5:
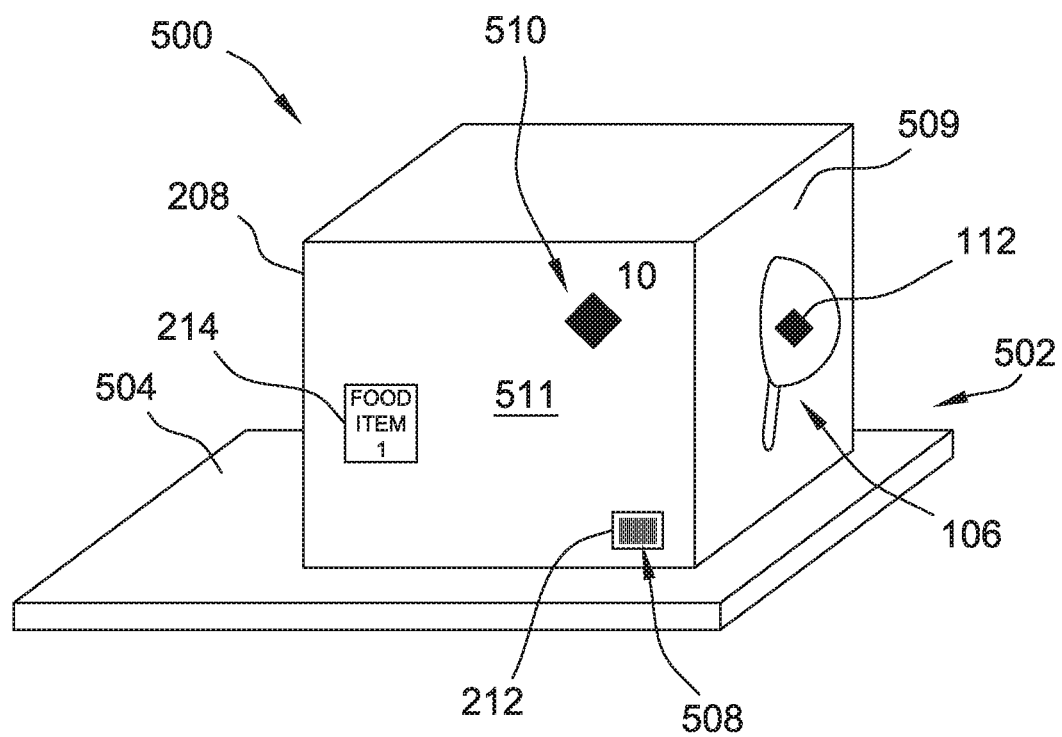
FIG. 5 is a diagram of an exemplary food packaging and display system that may be used with the systems shown in FIGS. 1 and 2.
Figure 5:
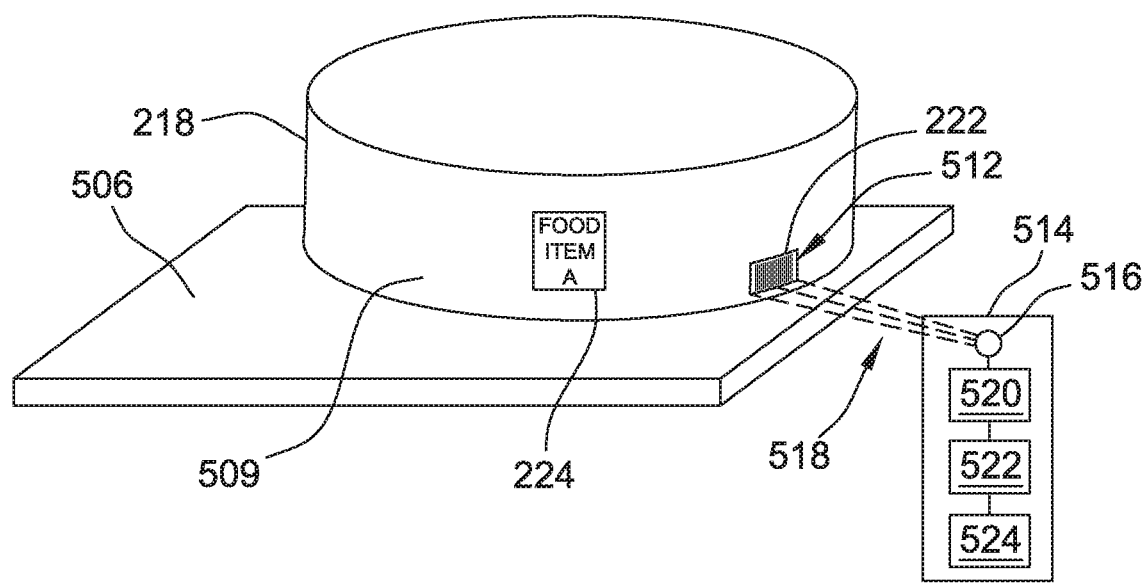

FIG. 5 is a diagram of an exemplary food packaging and display system 500 that may be used with system 100 and food service system 200 shown in FIGS. 1 and 2, respectively. In an exemplary embodiment, food packaging and display system 500 includes a display case 502 including, for example and without limitation, one or more shelves in at least one of a household cupboard, refrigerator, and a grocery store aisle. Also, in an exemplary embodiment, food packaging and display system 500 includes a plurality of shelves including a first shelf 504 and a second shelf 506 positioned beneath and proximate first shelf 504. First food container 208 is positioned upon first shelf 504 such that at least one of first-type third VI 212 and first-type fourth VI 214 is visible to a user of food packaging and display system 500 and system 100. Further, in an exemplary embodiment, first-type third VI 212 is embodied by a barcode 508 positioned on an exterior surface 509 of first food container 208 as, for example and without limitation, a label affixed thereto. In other embodiments, not shown, first-type third VI 212 is embodied by a diamond shape positioned upon exterior surface 509 of first food container 208, similarly to as shown and described above with reference to FIG. 2. In still other embodiments, first-type third VI 212 is embodied by both barcode 508 and the diamond shape affixed to exterior surface 509.

Also, in an exemplary embodiment, first food container 208 includes a first-type fifth VI 510 positioned on exterior surface 509 to indicate to users of food packaging and display system 500 and system 100 at least one of a total amount of calories and a number of servings transferable using first scoop 106 of first food item 102, contained in first food container 208. For example, and without limitation, first-type fifth VI 510 is embodied by a diamond shape identical to first-type first VI 112 with a "10" proximate the diamond shape and in a superscript position with respect thereto. As such, in an exemplary embodiment, first-type fifth VI 510 indicates to users of food packaging and display system 500 and system 100 that first food container 208 contains ten servings of first food item (e.g., "food item 1") transferable therefrom using first scoop 106. Further, in an exemplary embodiment, first scoop 106 is coupled to at least a portion of exterior surface 509 of first food container 208. In an exemplary embodiment, first scoop 106 is detachably coupled to exterior surface 509, as well as re-attachable thereto. In other embodiments, not shown, at least one scoop of the plurality of scoops of system 100 is not re-attachable to exterior surface 509, but rather food packaging and display system 500 is embodied by a set of a plurality of food containers where at least one scoop of the plurality of scoops is coupled to at least one respective food container for detachment by users prior to initiating use of food packaging and display system 500 and system 100. In still other embodiments, not shown, at least one scoop of the plurality of scoops of food packaging and display system 500 is coupled to a respective food container and is sold as is to a consumer at, for example, a grocery store. In yet other embodiments, not shown, at least one scoop (e.g., first scoop 106) of the plurality of scoops is enclosed in an interior of at least one food container (e.g., first food container 208) of the plurality of food containers, and such an enclosed scoop is removed by a user of at least one of system 100, food service system 200, and food packaging and display system 500 after opening a respective container of the plurality of containers having the enclosed scoop.

Further, in an exemplary embodiment, first food container 208 is embodied by a sealed container (e.g., at least one of a metal can, a glass jar, a glass bottle, a plastic and/or metal foil bag, and a vacuum packed plastic bag) configured to contain first food item 102 embodied by a pre-packaged food item 511 in an unprepared state (e.g., first food item 102 embodied by a raw uncooked "food item 1"). Where first food container 208 contains first food item 102 in an unprepared state, the amount of calories (e.g., first number of calories 130) is representative of the amount of calories of first food item 102 in the pre-packaged and unprepared (e.g., uncooked and/or not otherwise ready-to-eat from first food container 208) state.

Furthermore, in an exemplary embodiment, second food container 218 is positioned upon second shelf 506 such that at least one of second-type third VI 222 and second-type fourth VI 224 is visible to a user of food packaging and display system 500 and system 100. Moreover, in an alternative embodiment, second-type third VI 222 is embodied by a quick response (QR) code 512 positioned on exterior surface 509 of second food container 218 as, for example, and without limitation, a label affixed thereto. In other embodiments, not shown, second-type third VI 222 is embodied by a triangle shape positioned upon exterior surface 509 of second food container 218, similarly to as shown and described above with reference to FIG. 2. In still other embodiments, second-type third VI 222 is embodied by both QR code 512 and the triangle shape affixed to exterior surface 509. In yet other embodiments, not shown, second food container 218 also includes a second-type fifth VI configured similarly to first-type fifth VI 510 as shown and described above. Similarly, in an exemplary embodiment, at least one of first VI, second VI, fourth VI, and fifth VI includes at least one of barcode 508 and QR code 512 including, without limitation, at least one of alone and in combination with the various VI configurations shown and described above with reference to FIGS. 1 and 2.

Moreover, in an exemplary embodiment, at least one of system 100, food service system 200, and food packaging and display system 500 includes at least one of a QR code reader 514 and a barcode reader (not shown). QR code reader 514 is operable to read (e.g., through an optical sensor 516 such as a mobile phone camera) QR code 512 and acquire information contained (i.e., encoded) therein as data 518 (e.g., an optical signal). In other embodiments, not shown, QR code reader 514 is embodied by a barcode reader similarly operable in at least one of system 100, food service system 200, and food packaging and display system 500 to read barcode 508 and acquire information contained therein as data 518. In still other embodiments, not shown, QR code reader 514 is embodied by a multi-purpose reader device (e.g., smart phones and similar mobile computing and communications devices running at least one software application, i.e., "app", intended for use with at least one of system 100, food service system 200, and food packaging and display system 500) configured to at least one of read, acquire, and display information as data 518 contained in both of QR code 512 and barcode 508.

Also, in an exemplary embodiment, at least one of QR code reader 514 and barcode reader includes a computer-readable storage media (e.g., a memory 520), a processor 522 configured to execute software instructions from the computer-readable storage media, and a display 524 configured to enable, including in substantially real time, users of at least one of system 100, food service system 200, and food packaging and display system 500 to visualize data 518 in human-readable form including, without limitation, on display 524. Further, in an exemplary embodiment, human-readable data 518 is visible to users on display 524 after at least one of storage in memory 520 and processing by processor 522. Such human-readable data 518 includes, for example and without limitation, the amount of calories (e.g., second number of calories 138) contained in the respective internal volume (e.g., second internal volume 118, when substantially filled with second food item 104) of a respective scoop (e.g., second scoop 114) of the plurality of scoops of system 100. Human-readable data 518 also includes, for example and without limitation, a respective caloric food category (e.g., second caloric food category 140) of the plurality of different caloric food calories associated with the respective scoop. Furthermore, in an exemplary embodiment, human-readable data 518 includes, without limitation, a listing of food items (e.g., second listing of food items 142) belonging to the respective caloric food category (e.g., second caloric food category 140).

Further, in an exemplary embodiment, at least one of QR reader 514 and barcode reader is further operable to communicate, to at least one memory 520, processor 522, and display 524, data 518 encoded in at least one of QR code 512 and barcode 508 representative of the respective caloric food category (e.g., second caloric food category 140) associated with the respective scoop (e.g., second scoop 114). At least one of QR reader 514 and barcode reader is also further operable to communicate, to at least one memory 520, processor 522, and display 524, data 518 encoded in at least one of QR code 512 and barcode 508 representative of the listing of food items (e.g., second listing of food items 142) associated with the respective caloric food category (e.g., second caloric food category 140). Furthermore, in an exemplary embodiment, at least one of QR reader 514 and barcode reader is further operable to determine (i.e., using at least one of memory 520, processor 522, and display 524) at least one of at least one respective food item (e.g., second food item 104) belonging to the respective caloric food category (e.g., second caloric food category 140) and all food items belonging to at least one caloric food category of the plurality of different caloric food categories consumed by a user of at least one of system 100, food service system 200, and food packaging and display system 500 over a period of time (e.g., an integer multiple of at least one of a second, a minute, an hour, a day, a month, and a year).

Figure 6:
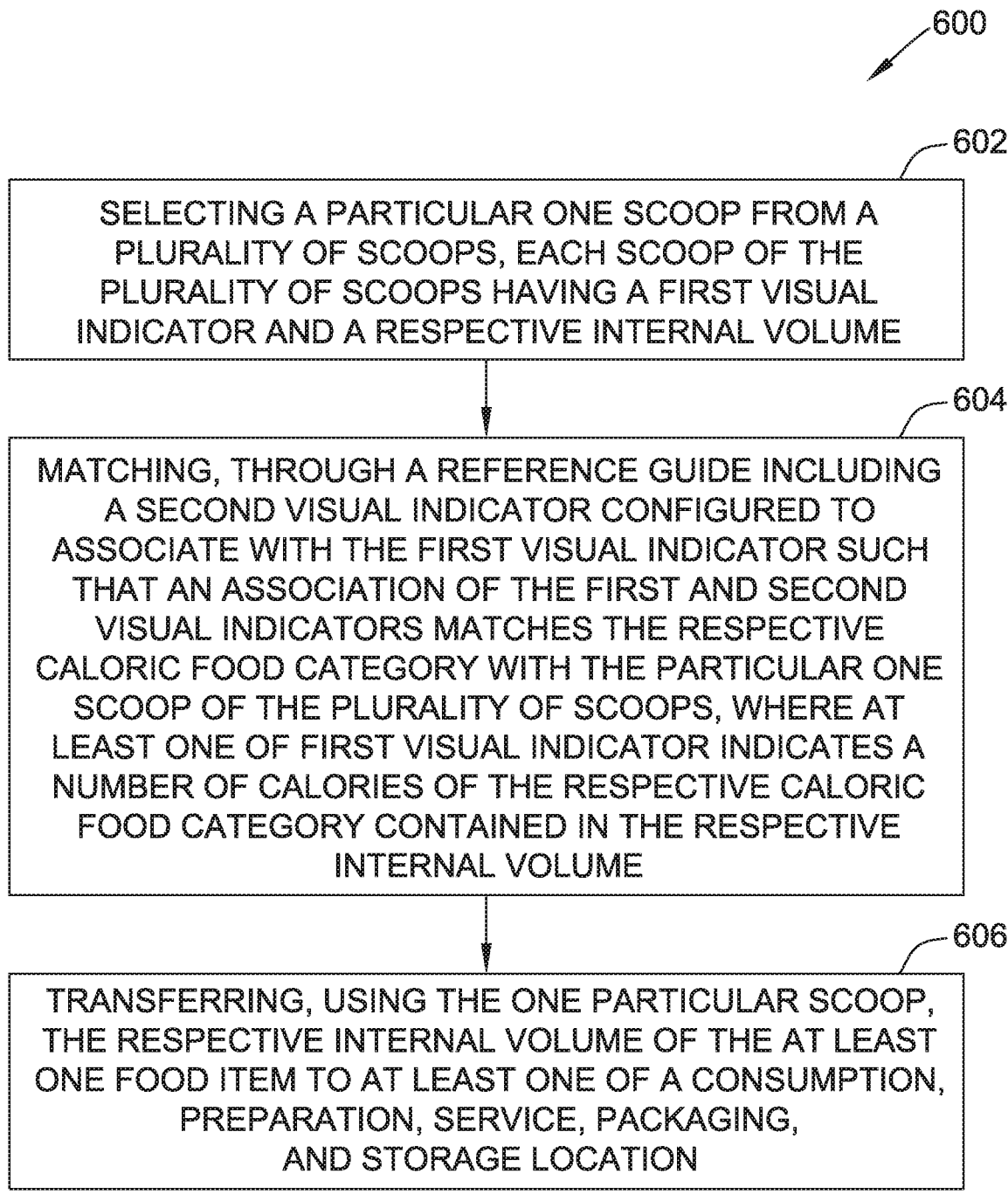
FIG. 6 is a flowchart of an exemplary method for quantifying calorie values for a plurality of different caloric food categories that may be used with the systems shown in FIGS. 1 and 2.

FIG. 6 is a flowchart of an exemplary method 600 for quantifying calorie values for a plurality of different caloric food categories that may be used with system 100 and food service system 200 shown in FIGS. 1 and 2, respectively. As shown and described above with reference to FIG. 1, in an exemplary embodiment, each caloric food category of the plurality of different caloric food categories is categorized based on volumetric calorie density of at least one food item (e.g., first food item 102) belonging to a respective caloric food category (e.g., first caloric food category 132) of the plurality of different caloric food categories. Also, in an exemplary embodiment, method 600 includes selecting 602 a particular one scoop (e.g., first scoop 106) from the plurality of scoops, where each scoop of the plurality of scoops has a first visual indicator (e.g., first-type first VI 112) and a respective internal volume (e.g., first internal volume 110).

Also, in an exemplary embodiment, method 600 includes matching 604 the first VI (e.g., first-type first VI 112) with reference guide 126 including a second VI (e.g., first-type second VI 128) configured such that an association of the first VI with the second VI matches a first caloric food category (e.g., first caloric food category 132) of the plurality of different caloric food categories with a first one scoop (e.g., first scoop 106) of the plurality of scoops, where at least one of the first VI and the second VI represents an amount of calories (e.g., first number of calories 130) of the first caloric food category contained in the respective internal volume (e.g., first internal volume 110) when the first one scoop is substantially filled with at least one food item (e.g., first food item 102) belonging to the first caloric food category. In the exemplary embodiment, selecting 602 is performed in method 600 prior to matching 604. In an alternative embodiment, not shown, matching 604 is performed in method 600 prior to selecting 602. Further, in an exemplary embodiment, method 600 includes transferring 606, using the first one scoop (e.g., first scoop 106), the respective internal volume (e.g., first internal volume 110) of at least one food item (e.g., first food item 102) belonging to the first caloric food category (e.g., first caloric food category 132) to at least one of a consumption, preparation, service, packaging, display, transport, sale, and storage location (e.g., location 144).

The above-described systems and methods for quantifying calorie values for a plurality of different caloric food categories are adaptable, without departing from the scope of the present Application, to quantifying other values of interest in foods including, without limitation, specific nutritive elements thereof. Thus, in alternative embodiments of system 100, food service system 200, and food packaging and display system 500, reference guide 124 and the VIs are configured such that an association of the first VI (e.g., first-type first VI 112) with the second VI (e.g., first-type second VI 128) matches a first food nutrient category of a plurality of different food nutrient categories with a first one (e.g., first scoop 106) of the plurality of scoops 300. Also, and analogously to systems 100, 200, and 500 shown and described above, at least one the first VI and the second VI represents an amount of a respective nutritive element of the first food nutrient category contained in the respective internal volume (e.g., first internal volume 110) when substantially filled with the first food nutrient category, where the respective nutritive element is one of sugar, fat, cholesterol, fiber, protein, and glycemic index. Also, similarly to systems 100, 200, and 500 shown and described above, at least one food item belonging to a respective food nutrient category of the plurality of different food nutrient categories has a substantially equal volumetric density of the respective nutritive element. For example, and without limitation, a first food nutrient category includes a first food item having a first mass of sugar contained in first internal volume 110 of first scoop 106, and a second food item having a second mass of sugar contained in first internal volume 110. When, as analogously described above with reference to FIG. 1, the tolerance (i.e., ±%) of first scoop 106 is ±5% of a round number (e.g., 10 grams (g)) for mass of sugar, the mass of sugar of either one or both of first and second food items contained in first internal volume 110 is ≥9.5 g and ≤10.5 g.

The above-described systems and methods for quantifying calorie values consumed of foods belonging to a plurality of different caloric food categories provide a more effective, less challenging, and less frustrating tool for people to control and quantify food caloric intake to achieve personal dietary goals over extended periods of time with a higher probability of success relative to known systems and methods. The above-described embodiments also facilitate categorization of a wide variety of food items based on volumetric calorie density rather than merely based on food groups. The above-described embodiments are further suited to providing greater selection of food items for use in a regimented, yet simplified dietary regime. The above-described systems and methods for quantifying calorie values consumed of foods belonging to a plurality of different caloric food categories are also suited to enabling a more cost-effective, less complex, and less time-consuming tool to achieve personal dietary goals of any type. The above-described embodiments are further suited to providing more accurate logging, counting, and tracking of food calories consumed over finite periods of time using a more uniform and standardized set of equipment implementable in any environment where foods are prepared, served, consumed, and purchased.

An exemplary technical effect of the methods, systems, and apparatus described herein includes at least one of: (a) increasing effectiveness, and reducing the complexity and time required for people to control and quantify food caloric intake to achieve personal dietary goals over extended periods of time with a higher probability of success relative to known systems and methods; (b) categorizing a wide variety of food items based on volumetric calorie density, rather than merely based on food groups; (c) increasing selection of food items for use in a regimented, yet simplified dietary regime; (d) reducing the cost and time necessary to achieve personal dietary goals of any type; and (e) enhancing the accuracy and efficiency of logging, counting, and tracking of food calories consumed over finite periods of time using a more uniform and standardized set of equipment implementable in any environment where foods are prepared, served, consumed, and purchased.

Exemplary embodiments of the above-described systems and methods for quantifying calorie values consumed of foods belonging to a plurality of different caloric food categories are not limited to the specific embodiments described herein, but rather, components of the devices and systems, and/or steps of the methods may be utilized independently and separately from other components and/or steps described herein. For example, the methods, systems, and apparatus may also be used in combination with other dietary control and quantification systems requiring improvements in performance, reduction in number of associated equipment pieces required, and enhancement of efficiency and versatility of manufacturing processes for such systems, and the associated methods are not limited to practice with only the systems and methods as described herein. Rather, exemplary embodiments can be implemented and utilized in connection with many other applications, equipment, and systems that may benefit from using the above-described embodiments of the above-described systems and methods for quantifying calorie values consumed of foods belonging to a plurality of different caloric food categories to improve the performance, reduce the size and/or weight, and enhance the versatility, effectiveness, and user success rates of food caloric intake control and quantification systems and methods and other related systems in various applications.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. The methods described herein may be encoded as executable instructions embodied in a computer-readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A system for quantifying calorie values for a plurality of different caloric food categories, said system comprising:
    a plurality of scoops, each scoop of the plurality of scoops comprising:
        a scoop body having a respective internal volume; and
        a first visual indicator; and
    a reference guide comprising a second visual indicator configured such that an association of the first visual indicator with the second visual indicator matches a first caloric food category of the plurality of different food caloric categories with a first one of the plurality of scoops, wherein:
        at least one of the first visual indicator and the second visual indicator represents an amount of calories of the first caloric food category contained in the respective internal volume when substantially filled with the first caloric food category.

2. The system according to claim 1, wherein the first visual indicator is identical to the second visual indicator.

3. The system according to claim 1, wherein the second visual indicator further indicates a listing of at least one food item belonging to a respective caloric food category of the plurality of different caloric food categories.

4. The system according to claim 1, wherein:
    a respective caloric food category of the plurality of different caloric food categories is categorized based on a volumetric calorie density of at least one food item belonging to the respective caloric food category;

each scoop of the plurality of scoops has a different respective internal volume; and the amount of calories of each respective food item belonging to the respective caloric food category contained in the respective internal volume is substantially equal.

5. The system according to claim 1, wherein the amount of calories of at least one food item belonging to a respective caloric food category of the plurality of different caloric food categories contained in the respective internal volume is within a predetermined percentage of a round number of calories.

6. The system according to claim 5, wherein the round number of calories is an integer multiple of at least one of 10 (ten) calories and 5 (five) calories.

7. The system according to claim 5, wherein the round number of calories contained in the respective internal volume of each scoop of the plurality of scoops is substantially equal.

8. The system according to claim 5, wherein the predetermined percentage is greater than 5% (five percent) and less than or equal to 10% (ten percent).

9. The system according to claim 1, wherein at least one of the first visual indicator and the second visual indicator is positioned on the scoop body.

10. The system according to claim 1, wherein the scoop body of at least one scoop of the plurality of scoops comprises a handle coupled thereto.

11. The system according to claim 10, wherein at least one of the first visual indicator and the second visual indicator is positioned on the handle.

12. The system according to claim 11, wherein the first visual indicator comprises at least one of:
a color;
an alphanumeric symbol including at least one of a letter, a number, and a word;
a graphic symbol;
a shape defined by the scoop body; and
a shape defined by the handle.

13. The system according to claim 1, wherein the reference guide is positioned on the scoop body.

14. The system according to claim 1, wherein the scoop body comprises at least one mark configured to indicate at least one fractional value of the amount of calories contained in the respective internal volume.

15. The system according to claim 1, wherein at least one of the first visual indicator and the second visual indicator is at least one of removable, detachable, editable, reusable, and replaceable from at least one scoop of the plurality of scoops.

16. The system according to claim 1, wherein the first visual indicator comprises at least one of:
a color;
an alphanumeric symbol including at least one of a letter, a number, and a word;
a graphic symbol; and
a shape defined by the scoop body.

17. The system according to claim 1, wherein the first visual indicator comprises at least one of a barcode and a quick response (QR) code, said system further comprising at least one of a barcode reader and a QR code reader operable to read data encoded by at least one of the barcode and the QR code and to indicate at least one of:
the amount of calories contained in the respective internal volume of a respective scoop of the plurality of scoops;
a respective caloric food category of the plurality of different caloric food categories associated with the respective scoop; and
a listing of food items belonging to the respective caloric food category.

18. The system according to claim 17, wherein at least one of the barcode reader and the QR code reader is further operable to at least one of:
communicate, to at least one of a processor, a memory, and a display, data representative of at least one of:
the respective caloric food category associated with the respective scoop; and
the listing of food items associated with the respective caloric food category; and
determine a total amount of calories consumed of at least one of:
at least one respective food item belonging to the respective caloric food category; and
all food items belonging to at least one caloric food category of the plurality of different caloric food categories consumed over a period of time including an integer multiple of at least one of a second, a minute, an hour, a day, a week, a month, and a year.

19. The system according to claim 1 further comprising a plurality of food containers, each food container of the plurality of food containers configured to contain at least one respective food item belonging to at least one respective caloric food category of the plurality of different caloric food categories, each food container comprising:
a container body; and
a third visual indicator identical to the first visual indicator, wherein the third visual indicator indicates the amount of calories of the one respective food item contained in the respective internal volume.

20. The system according to claim 19, wherein at least one scoop of the plurality of scoops is coupled to at least one food container of the plurality of food containers.

21. The system according to claim 19, wherein at least one food container of the plurality of food containers is a sealed container configured to contain one pre-packaged food item belonging to the respective caloric food category therein, and wherein the amount of calories is representative of an amount of calories of the one pre-packaged food item.

22. The system according to claim 19, wherein at least one food container of the plurality of food containers is configured to contain one prepared food item belonging to the respective caloric food category therein, and wherein the amount of calories is representative of an amount of calories of the one prepared food item.

23. The system according to claim 19, wherein at least one food container of the plurality of food containers is configured to contain one unprepared food item belonging to the respective caloric food category therein, and wherein the amount of calories is representative of an amount of calories of the one unprepared food item.

24. The system according to claim 19, wherein the third visual indicator is at least one of removable, detachable, editable, reusable, and replaceable from at least one food container of the plurality of food containers.

25. The system according to claim 19, wherein at least one food container of the plurality of food containers further comprises a fourth visual indicator indicating an identity of the one respective food item contained therein.

26. The system according to claim 25, wherein the fourth visual indicator is at least one of removable, detachable, editable, reusable, and replaceable from at least one food container of the plurality of food containers.

27. The system according to claim 19 further comprising at least one surface and at least one supportive member, the at least one supportive member configured to elevate and support the at least one surface above a walking surface, wherein the plurality of food containers are viewable from the walking surface and positioned at least one of upon and at least partially through the at least one surface.

28. The system according to claim 27, wherein at least one scoop of the plurality of scoops is coupled to at least one of the at least one surface, the at least one supportive member, and at least one food container of the plurality of food containers.

29. The system according to claim 1, wherein the plurality of scoops comprises at least two separate and distinct scoop bodies.

30. The system according to claim 1, wherein:
the plurality of scoops comprises at least one single integral scoop body; and
the single integral scoop body comprises a first scoop and a second scoop, wherein:
the first scoop is defined by a first graduation on the single integral scoop body; and
the second scoop is defined by a second graduation on the single integral scoop body, and wherein the first graduation is located at a different location on the single integral scoop body from the second graduation.

31. The system according to claim 1, wherein the plurality of different caloric food categories includes the first caloric food category and a second caloric food category, wherein at least one scoop of the plurality of scoops comprises a multiple food category scoop, the scoop body of the multiple food category scoop having:
a first internal volume substantially equal to the respective internal volume;
a second internal volume less than the first internal volume;
a plurality of graduations including a first graduation positioned on the scoop body to indicate a first location thereupon corresponding to the first internal volume, the plurality of graduations further including a second graduation positioned on the scoop body to indicate a second location thereupon corresponding to the second internal volume; and
a plurality of first visual indicators including a first-type first visual indicator positioned proximate the first graduation, the first-type first visual indicator representing the amount of calories of the first caloric food category, the plurality of first visual indicators further including a second-type first visual indicator positioned proximate the second graduation, wherein the second-type first visual indicator is different from the first-type first visual indicator, and wherein:
the first-type first visual indicator represents a first amount of calories of the first caloric food category contained in the first internal volume when the scoop body is filled with the first caloric food category to a first level substantially equal to the first graduation; and
the second-type first visual indicator represents a second amount of calories of the second caloric food category contained in the second internal volume when the scoop body is filled with the second caloric food category to a second level substantially equal to the second graduation.

32. A method for quantifying food calorie values for a plurality of different caloric food categories, each caloric food category of the plurality of different caloric food categories categorized based on a volumetric calorie density of at least one food item belonging to a respective caloric food category of the plurality of different caloric food categories, said method comprising:
selecting a particular one scoop from a plurality of scoops, each scoop of the plurality of scoops having a first visual indicator and a respective internal volume;
matching the first visual indicator with a reference guide including a second visual indicator configured such that an association of the first visual indicator with the second visual indicator matches a first caloric food category of the plurality of different caloric food categories with a first one scoop of the plurality of scoops, wherein at least one of the first visual indicator and the second visual indicator represents an amount of calories of the first caloric food category contained in the respective internal volume when substantially filled with the first caloric food category; and
transferring, using the first one scoop, the respective internal volume of at least one food item belonging to the first caloric food category to at least one of a consumption, preparation, service, packaging, display, transport, sale, and storage location.

33. A system for quantifying nutritive element values for a plurality of different food nutrient categories, said system comprising:
a plurality of scoops, each scoop of the plurality of scoops comprising:
a scoop body having a respective internal volume; and
a first visual indicator; and
a reference guide comprising a second visual indicator configured such that an association of the first visual indicator with the second visual indicator matches a first food nutrient category of the plurality of different food nutrient categories with a first one of the plurality of scoops, wherein:
at least one of the first visual indicator and the second visual indicator represents an amount of a respective nutritive element of the first food nutrient category contained in the respective internal volume when substantially filled with the first food nutrient category, and wherein the respective nutritive element is one of sugar, fat, cholesterol, fiber, protein, and glycemic index.

* * * * *